United States Patent
Mellars et al.

(10) Patent No.: US 10,001,499 B2
(45) Date of Patent: Jun. 19, 2018

(54) MODULAR WORKCELLS FOR LAB AUTOMATION

(71) Applicants: Colin Mellars, Dover, NJ (US); Baris Yagci, Whippany, NJ (US); Benjamin S. Pollack, Budd Lake, NJ (US)

(72) Inventors: Colin Mellars, Dover, NJ (US); Baris Yagci, Whippany, NJ (US); Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 306 days.

(21) Appl. No.: 14/434,580

(22) PCT Filed: Oct. 11, 2013

(86) PCT No.: PCT/US2013/064630
§ 371 (c)(1),
(2) Date: Apr. 9, 2015

(87) PCT Pub. No.: WO2014/059330
PCT Pub. Date: Apr. 17, 2014

(65) Prior Publication Data
US 2015/0276775 A1    Oct. 1, 2015

Related U.S. Application Data

(60) Provisional application No. 61/712,676, filed on Oct. 11, 2012.

(51) Int. Cl.
    *G01N 35/02* (2006.01)
    *G01N 35/04* (2006.01)
    *G01N 35/00* (2006.01)

(52) U.S. Cl.
    CPC ....... *G01N 35/026* (2013.01); *G01N 35/0092* (2013.01); *G01N 35/0099* (2013.01); *G01N 35/04* (2013.01); *G01N 2035/00326* (2013.01); *G01N 2035/047* (2013.01)

(58) Field of Classification Search
    CPC ... G01N 2035/00801; G01N 2035/041; G01N 2035/047; G01N 2035/0472; G01N 2035/0424; G01N 2035/0444; G01N 2035/0446; G01N 2035/0453;
    (Continued)

(56) References Cited

U.S. PATENT DOCUMENTS

| 6,202,829 B1 | 3/2001 | Van Dyke et al. |
| 2002/0147515 A1 | 10/2002 | Fava et al. |

(Continued)

FOREIGN PATENT DOCUMENTS

EP    2455763 A1    5/2012

OTHER PUBLICATIONS

PCT International Search Report and Written Opinion dated Apr. 23, 2014 (7 Pages).

*Primary Examiner* — Erik B Crawford

(57) ABSTRACT

Systems and methods are provided for performing a work-flow, which may be in an IVD environment. A plurality of workcells can be used to perform tasks, while vessels can be automatically transported between the workcells using bulk transport trays along an inter-cell track, allowing each workcell to be independently adapted to one or more tasks in the work-flow.

5 Claims, 15 Drawing Sheets

(58) Field of Classification Search
CPC .............. G01N 35/021; G01N 35/026; G01N 35/0092; B01L 9/52; Y10T 436/113332
See application file for complete search history.

(56) References Cited

U.S. PATENT DOCUMENTS

| | | | |
|---|---|---|---|
| 2005/0013737 A1* | 1/2005 | Chow | G01N 35/025 422/63 |
| 2008/0190735 A1* | 8/2008 | Luoma | B01L 9/00 198/340 |
| 2009/0247417 A1 | 10/2009 | Haas et al. | |
| 2013/0125675 A1* | 5/2013 | Muller | B01D 21/262 73/864.23 |

* cited by examiner

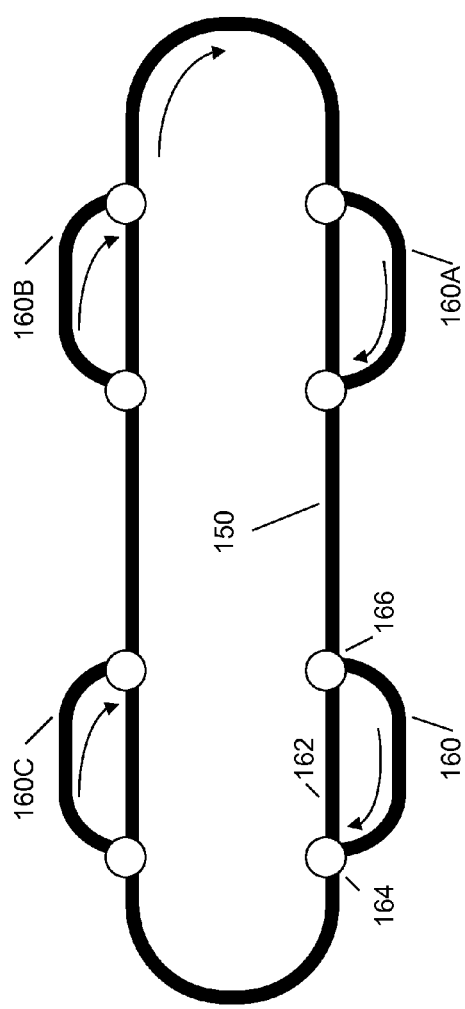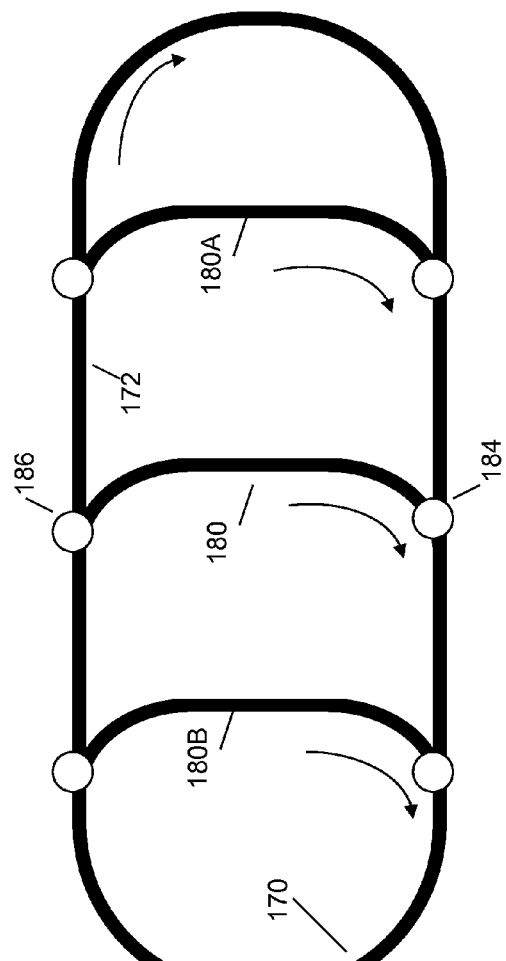

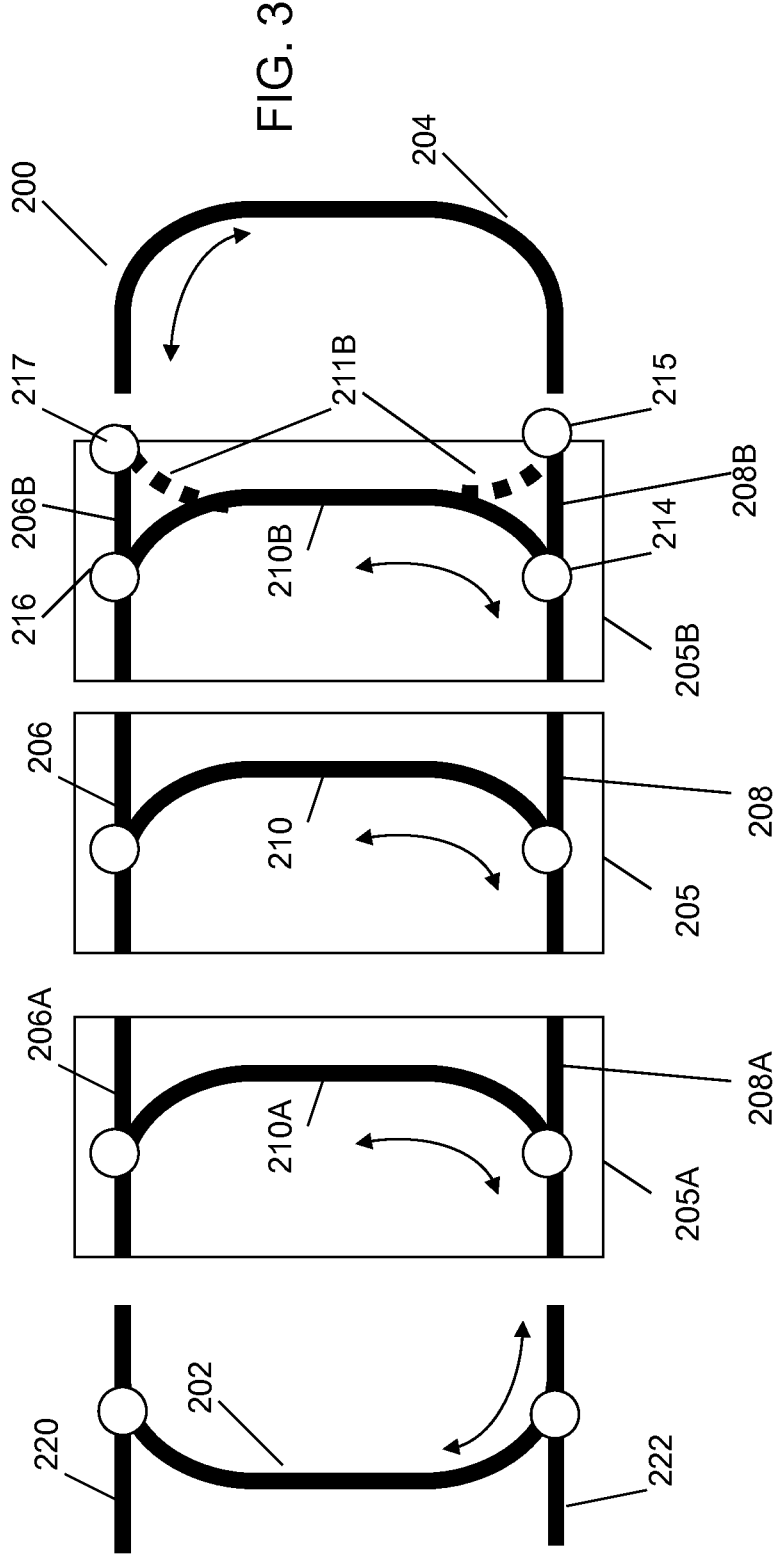

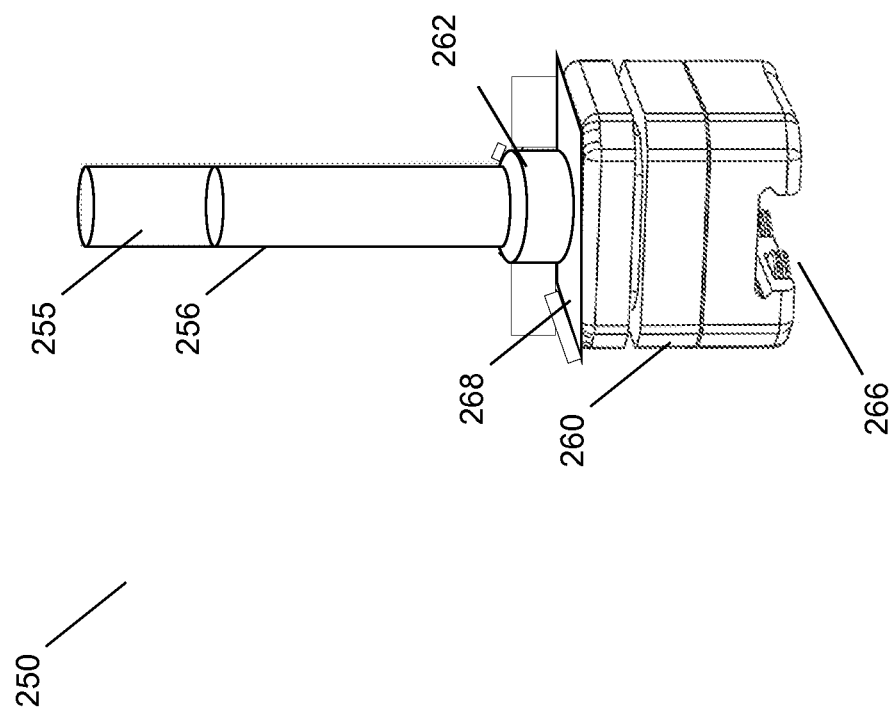

MODULAR WORKCELLS FOR LAB AUTOMATION

CROSS-REFERENCE TO RELATED APPLICATIONS

This application claims priority to U.S. provisional application Ser. No. 61/712,676 filed Oct. 11, 2012, which is incorporated herein by reference in its entirety.

TECHNOLOGY FIELD

The present invention relates in general to an automation system for use in a laboratory environment and, more particularly, to systems and methods for transporting pluralities of samples between workcells in a laboratory. Embodiments of the present invention are particularly well suited, but in no way limited, to the use of workcells and tray to transport patient samples between those workcells.

BACKGROUND

In-vitro diagnostics (IVD) allows labs to assist in the diagnosis of disease based on assays performed on patient fluid samples. IVD includes various types of analytic tests and assays related to patient diagnosis and therapy that can be performed by analysis of a liquid sample taken from a patient's bodily fluids, or abscesses. These assays are typically conducted with automated clinical chemistry analyzers ("analyzers") onto which fluid containers, such as tubes or vials containing patient samples, have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available.

These lab automation systems, however, often use individual pucks to transport samples within an analyzer, utilizing a single track. While this track can have branches to direct selected carriers to stations within the analyzer, these systems still rely on main track, which may be a unidirectional loop or bidirectional linear track. While this arrangement may be suitable for smaller laboratories, relying on a single track to transport thousands of samples per hour can limit scalability of the system. As the number of samples per hour being processed by the system goes up, the number of samples traversing the automation track also increases. Similarly, in prior art systems, the size of the track can also increase, causing the larger number of samples to also spend more time on the automation tracks. This can cause the automation track to become a performance bottleneck.

Some prior art systems have mitigated this issue by using carriers that hold more than one sample as the carriers traverse the automation system. While this can reduce the number of carriers on the track, all samples in each multi-sample carrier must go to all locations within the system where a single sample might need to go, which can increase the amount of time a carrier spends on the track. Meanwhile, the track that must be traversed still grows with the number of stations provided. Scalability is still limited. Accordingly, it is desirable to have an automation system that allows greater scalability as a lab grows.

SUMMARY

Embodiments of the present invention can overcome one or more of the above shortcomings and drawbacks by providing workcells within an automation system. Each workcell can be individually tailored to provide at least one of a pre-processing step, a processing step, or a post-processing step, as part of a larger work-flow. Each workcell may include specialized or redundant systems to facilitate one or more tasks. An inter-cell track suitable for transporting tray holding a plurality of vessels can provide bulk transport between workcells to create a work-flow. Each workcell can use an internal automation mechanism suitable to the task performed, which may be different than the mechanism used in other workcells and may enable legacy automation systems to be used. This technology is particularly well-suited for, but by no means limited to, transport mechanisms in an automation system for use in an in-vitro diagnostics (IVD) environment.

According to one embodiment of the invention, a system for performing in-vitro diagnostics includes a plurality of workcells comprising a first and a second workcell, each suitable for performing one or more tasks in a work-flow and an inter-cell track configured to provide one or more paths for transporting vessels between the plurality of workcells. A first tray can be configured to hold a first plurality of vessels and transport the along the inter-cell track from the first workcells to the second workcell, while one or more controllers can be configured to automatically causing the plurality of vessels to be loaded into the first tray from the first workcell upon completion of a first task at the first workcell and directing the one or more trays to the second workcell.

According to one aspect, the first workcell can include a plurality of carriers, each configured to hold at least a subset of the plurality of vessels and an internal automation track that is configured to guide the plurality of carriers within the first workcell to a plurality of locations to perform the one or more tasks. According to another aspect, a robot arm can be configured to remove each of the plurality of vessels from the plurality of carriers and place the vessels into the first tray. According to yet another aspect, the first tray can be configured to hold a first maximum number of vessels and each carrier is configured to hold second maximum number of vessels, which is substantially less than the first maximum number of vessels. In another aspect, the first tray can be configured to hold the plurality of carriers along with the plurality of vessels and to transfer the plurality carriers to the second workcell.

According to another aspect, the system includes a plurality of trays that include the first tray; the plurality of trays can be configured to transport a second plurality of vessels, of which the first plurality of vessels is part, between the plurality of workcells. According to yet another aspect, the plurality of workcells include at least one pre-analytic workcell, at least one analytics workcell, and at least one post-analytic workcell. According to still another aspect, the first workcell can include at least one station configured to perform at least one of: decapping the plurality of vessels; immunoassays on patient samples contained in the plurality of vessels; automated chemical analysis on patient samples contained in the plurality of vessels; and automated hematological analysis on patient samples contained in the plurality of vessels. According to another aspect, the second workcell can include at least one station configured to perform at least one of: immunoassay on patient samples contained in the plurality of vessels; automated chemical analysis on the patient samples; automated hematological analysis on the patient samples; and preparing the patient samples for storage.

According to another embodiment of the invention, an automation system for facilitating an in-vitro diagnostics work-flow includes a track configured to provide one or more paths for transporting vessels between a plurality of workcells, a plurality of trays, each configured to receive a first plurality of vessels from a first workcell and to transport the vessels along the track to a second workcell and a loading mechanism. The loading mechanism can be configured to perform one of: loading the plurality of vessels from carriers within the first workcell to the plurality of trays and unloading the plurality of vessels from the plurality of trays to carriers within the second workcell, wherein the plurality of trays are configured to hold more vessels than each individual carrier.

According to one aspect, the system includes one or more processors configured to schedule the plurality of trays along the track and automatically directing the trays between the plurality of workcells. According to another aspect, the track is configure to transport vessels between the plurality of workcells as part of a work-flow, including performing a pre-analytic step, an analytics step, and a post-analytic step, each performed at separate ones of the plurality of workcells. According to yet another aspect, the track can be configured to transport vessels between the plurality of workcells as part of a work-flow including at least two of: decapping the plurality of vessels; performing immunoassays on patient samples contained in the plurality of vessels; performing automated chemical analysis on patient samples contained in the plurality of vessels; and performing automated hematological analysis on patient samples contained in the plurality of vessels.

According to another embodiment of the invention, a method for performing in-vitro diagnostics includes steps of performing a first task in a work-flow on a plurality of samples, using a first workcell and automatically loading the plurality of vessels from the first workcell to a first tray on an inter-cell track, which is configured to provide one or more paths for transporting a plurality of vessels, each containing one of the plurality of samples, between a plurality of workcells. The method includes moving the first tray along the track to a second workcell, automatically unloading the plurality of vessels into the second workcell and performing a second task in a work-flow on the plurality of samples, using the second workcell. The plurality of vessels can be transported within at least one of the first and second workcells by a plurality of carriers, and each of the plurality of carriers is configured to hold less than the entire plurality of vessels.

According to one aspect, the method includes the step of transporting the plurality of carriers, using a track internal to the first or second workcell, to a plurality of stations configured to perform the first or second task. According to another aspect, the step of loading is performed using a robot arm configured to remove vessels from the plurality of carriers and place each vessel into the first tray. According to yet another aspect, the step of loading is performed by moving the plurality of carriers, holding the plurality of vessels, into the first tray. According to still another aspect, the method includes using a processor to automatically schedule the motion of a plurality of trays, of which the first tray is a member between a plurality of workcells, of which the first and second workcells are members.

According to one aspect, the first task is one of: decapping the plurality of vessels; performing immunoassays on patient samples contained in the plurality of vessels; performing chemical analysis on patient samples contained in the plurality of vessels; and performing hematological analysis on patient samples contained in the plurality of vessels. According to another aspect, the first task is one of: performing immunoassays on patient samples contained in the plurality of vessels; performing chemical analysis on the patient samples; performing hematological analysis on the patient samples; and preparing the patient samples for storage.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 3 is a diagrammatic view of an exemplary modular track configuration that can be used with the embodiments disclosed herein;

FIG. 4A is a perspective view of an exemplary carrier that can be used with the embodiments disclosed herein;

DETAILED DESCRIPTION OF ILLUSTRATIVE EMBODIMENTS

Figure 1:
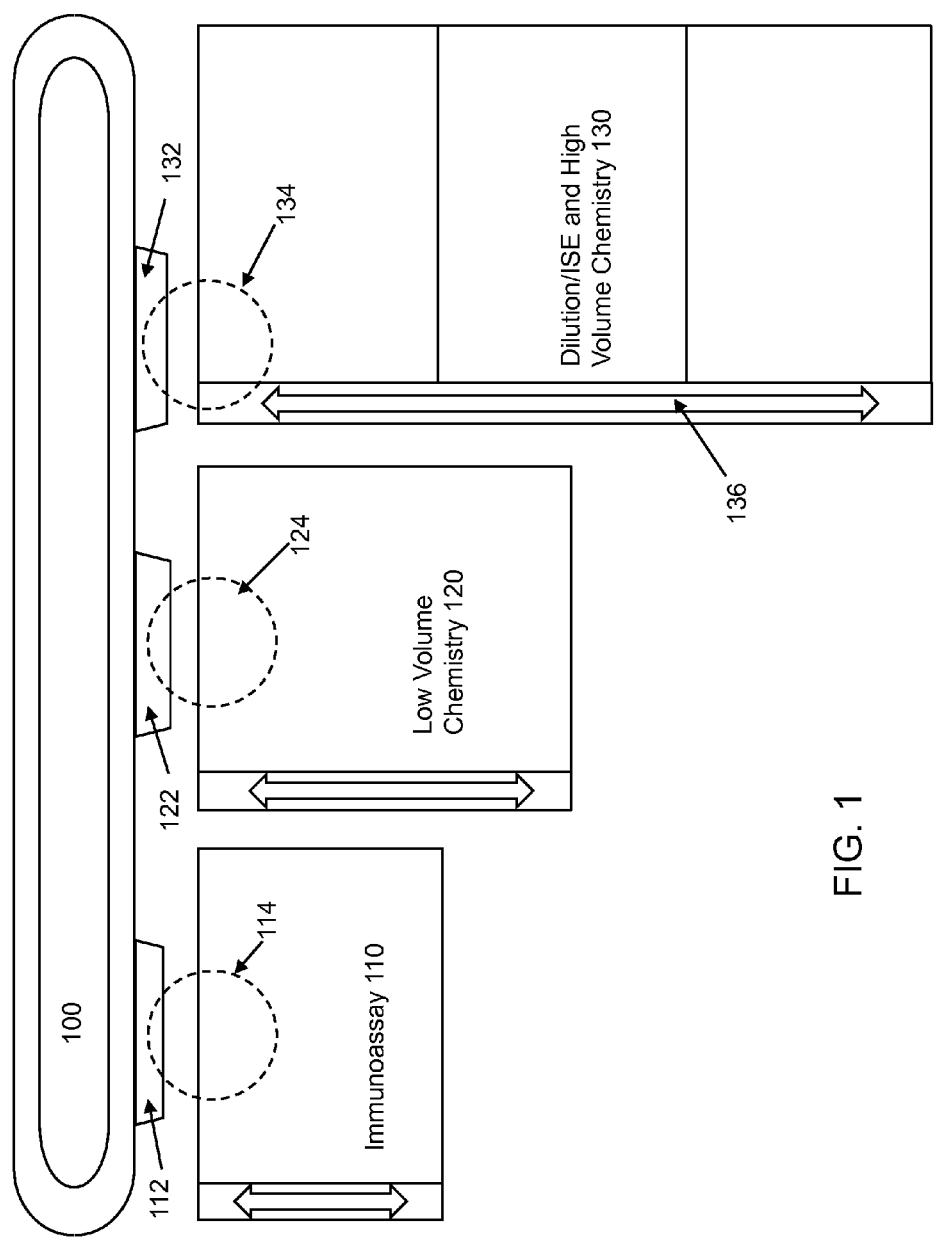
FIG. 1 is a top view of an exemplary clinical chemistry analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassay chemistry tests, or other observable tests on each sample. The term analyzer may refer to, but is not limited to, an analyzer that is configured as a modular analytical system. A modular analytical system includes an integrated and extendable system comprising any combination of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surface suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different section of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or workcells.

Module: A module performs specific task(s) or function(s) within a modular analytical system. Examples of modules may include: a pre-analytic module, which prepare a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

The above problems in the prior art have motivated the discovery of improve apparatus and methods for providing workcells within an in-vitro diagnostics lab that utilize separate local and inter-cell automation system. Stations within an automated clinical analyzer ("analyzer") can be broken into local workcells based on functionality. Each workcell can include one or more stations or modules from an analyzer suitable for performing one or more tasks that are part of a larger work-flow, and may include standalone analyzers. By breaking the overall analyzer into a series of workcells, traffic in a given area of analyzer can be segregated into those samples that are most relevant to that portion of the analyzer. For example, if an analyzer has a clinical chemistry workcell, the systems described herein can be used to deliver only samples that are ready and have a need for clinical chemistry analysis.

An inter-cell track can be used to shuttle trays of samples between workcells. The inter-cell track allows samples to be routed through the analyzer during a work-flow in hierarchical manner and allows scalable workcells to be created that specialize in certain work-flow tasks. Related tasks of the work-flow can be performed within a single workcell allowing local resources to be specialized to adapt to those tasks. When a sample is ready for a next task in the work-flow that can be performed by another workcell, the sample may be placed in a tray to be shuttled to the next workcell. Within each workcell, samples may be routed in any suitable manner, such as using individual pucks. Between workcells, larger trays can be used to facilitate bulk transfer of samples between workcells.

For example, a work-flow may include pre-analytic tasks, one or more analytic tasks, and post-analytic tasks. Pre-analytic tasks can include preparing the sample for analysis. This can include, but is not limited to, removing the cap from the sample tube, storing any contents, centrifuging a sample to settle out precipitates, or adding any stabilizers or other reagents, such as declotting factors to whole blood samples. Analytic tasks can be any suitable analysis task that is performed by an analyzer. Exemplary tasks include, but are not limited to, performing chemical analysis, immunoassays, hematological analysis of the sample, etc. Post-analytic steps can include preparing the sample for storage. This may include, but are not limited to, recapping sample tubes, adding any stabilizing reagents necessary for storage, moving the sample to a refrigerated storage area, or moving the sample to an output lane to be retrieved by an operator.

By utilizing workcells and an inter-cell track that uses bulk transfer of samples, local traffic can be scheduled and routed using different mechanisms than the mechanisms used to send samples between cells. By using a bulk transfer tray between cell greater scalability may be achieved. The use of both local automation systems and inter-cell bulk transfer can be likened to a mature national transit system. Local automation systems may utilize a plurality of carriers that transport one or a few samples at a time and act like cars or taxis, allowing individuals to randomly access local locations. Meanwhile, the inter-cell automation can act like airplanes, buses, or trains, carrying samples in bulk between local areas with less traffic.

In the prior art, as the number of stations within an analyzer grows, the track used to handle individual samples and other carriers also grows proportionally. This requires long tracks, where each sample traverses each point on the main track. In order to increase the throughput of an analyzer, more stations would need to be added, increasing the total number of samples that must traverse each point on any main section of the track. As a result, in order to increase throughput the number of individual samples that must traverse a individual point on the track needs to be increased. Conventional track systems are limited by the speed of carriers on the track. Therefore, conventional track systems utilizing individual carriers quickly approached natural limits of the tracks, making scalability impossible beyond a certain throughput. By utilizing workcells and inter-cell track, the present invention can overcome the scalability issues of the prior art.

One way that the workcell concept improves scalability is that redundancy can easily be added to a system, allowing load-balancing without placing proportional burdens on track resources. For example, multiple pre-analytic workcells can be used. Within each of the multiple pre-analytic workcells, the throughput may be limited by the local automation track used within each workcell. However, by using a plurality of pre-analytic workcells, the overall throughput can increase proportionally to the number of workcells used. Once samples finish the pre-analytic tasks and pre-analytic workcells, they may then be loaded into bulk transfer trays and traverse the inter-cell track. Some trays may be loaded with samples destined for hematological workcells, while some may be destined for immunoassay workcells, and/or clinical chemistry workcells.

By utilizing trays holding a plurality of samples on the inter-cell track, the number of trays that must traverse any given point on the inter-cell track per hour can be decreased proportionally to the size of the trays. For example, if the requirements of a laboratory require 10,000 samples per hour to be processed and each pre-analytic of five workcell can handle 2000 samples per hour, trays can be used that hold 20 samples to reduce the number of trays that must traverse the inter-cell track from the pre-analytic workcells to 500 trays per hour. Whereas a traditional, non-hierarchical approach to automating samples would require that nearly three samples traverse a single point in the automation track per second, this exemplary inter-cell track need only transport one tray every seven seconds. Moreover, because these 500 trays per hour are servicing five pre-analytic workcells, each pre-analytic workcell need only load and send 100 trays per hour.

Meanwhile, because samples held in inter-cell trays can be unloaded at a destination workcell, the destination workcell may use a different automation approach than the pre-analytic workcell. For example, a pre-analytic workcell may use a FIFO approach to de-capping and preparing each sample for analysis. Traditional friction-based tracks and passive pucks may be used to reduce the cost of that automation system. Meanwhile, an analytic workcell may utilize a series of immunoassay stations and clinical chemistry stations. Within the analytic workcell, routing may require random access to samples as analysis stations prepare to handle each required test for each sample. The local automation system for the analytic workcell may utilize a more advanced automation track within the workcell, such as intelligent autonomous carriers operating on a magnetic track. Such an automation system, as well as other suitable automation systems that can be used for local automation systems within a workcell, are explained in further detail in U.S. Patent Application Ser. No. 61/594,476, filed Feb. 3, 2012, which is incorporated herein by reference in its entirety.

An inter-cell track can also allow physical scalability of an analyzer. By utilizing a plurality of workcells, individual workcells may be located in different areas of the lab.

Whereas traditional automation systems for in-vitro diagnostics (IVD) necessitate placing all stations served by the automation system in close proximity to one another, and inter-cell track may allow individual workcells to be placed on different ends of a lab, in different rooms within a building, or even on different floors. Because the inter-cell track utilizes bulk transfer of carriers using trays having a plurality of slots, the inter-cell track may be able to operate at a slower rate of speed, then local automation systems within each workcell. These slower tracks may utilize cheaper track designs, such as passive tracks along which trays are driven, or friction tracks, which drive carriers at a reasonable rate of speed. This can allow long sections of inter-cell track to be used without greatly increasing the cost of an analyzer.

By utilizing workcells and an inter-cell track, an entire laboratory may effectively become one analyzer that is fully automated. Many prior art automation systems are limited to local automation systems, such as an automation system within an analyzer that performs only analytic tasks. Pre-analytic steps, such as decapping, stirring samples, etc. are often performed by hand or by utilizing a standalone preprocessing station. Once samples a preprocessed, operators often manually carry trays of samples across a lab to be inserted by hand into an analyzer. Accordingly, many prior art laboratories included a plurality of standalone machines, some of which had limited local automation. By utilizing workcells and an inter-cell track in accordance with embodiments of the present invention, the machines in a laboratory can be integrated into a single automation system that automates the entire process for performing analysis on samples.

Furthermore, it should be appreciated that the interface between the inter-cell track (which uses trays) and each workcell (which use local carriers) can be used to retrofit existing standalone infrastructure into a workcell-based. The interface between inter-cell track and each workcell can be used to remove samples from an inter-cell tray and place the samples automatically into any reasonable local automation system. For example, where an existing workstation may utilize a friction-based track with passive pucks, the interface between inter-cell track and the friction track may include a robot arm that places and removes sample containers, such as test tubes, into and out of the friction pucks of the local automation system and the slots of the tray. Similarly, other workcells may utilize different local automation approaches and may be interfaced with a similar robot arm for loading and unloading sample vessels from the tray into the local automation system.

By allowing existing laboratory equipment to be used with the inter-cell track the upgrade cost of moving to a workcell-based automation approach can be mitigated. By utilizing the inter-cell track, rather than requiring manual efforts of operators, the number of operators in the lab can be reduced and the cost per sample may be reduced.

Local Automation Systems

An exemplary track geometry for use in transporting samples within an analyzer typical in prior art configurations, and adaptable to the present invention, is shown in FIG. 1. This track can include prior art friction tracks. Track 100 can be a generally oval shaped track that conveys samples in pucks or trays between various stations, such as sample preparation or analyzing/testing stations 110, 120, and 130. Each of the analyzer/testing stations 110, 120, and 130 may be part of a single workcell, or may serve as individual workcells, if track 100 is adapted to be an inter-cell track utilizing trays. If used as workcell stations 110, 120, and 130 can utilize local automation tracks, such as track 136, to shuttle samples within the workcell utilizing individual carriers that each transport one patient sample (or more samples). Meanwhile, if track 100 is adapted to be an inter-cell track, trays containing multiple samples can be utilized to move samples between each of the stations 110, 120, and 130.

For illustrative purposes, the system shown in FIG. 1 will be discussed as a traditional local automation system, whereby individual carriers, each holding one sample traverse track 100 and access the various stations. This can form a single workcell. Track 100 could be a single direction track or, in some instances, a linear bidirectional track. In this exemplary set-up, each analyzer station 110, 120, and 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station or stations 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub modules of high-volume chemistry station 130.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a local track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track on segment 172 or be diverted onto path 180. Once an analyzer station along handling path 180 is done processing the sample, the sample proceeds to decision point 184 where it may be placed back onto the main path 170.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular component that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B be a module that performs ISE electrolyte testing, like module 130 (FIG. 1). In this example, the main outer track can be formed by track segments 202, 204, 206, 206A, 206B, 208, 208, and 208B. Within the analyzer modules 205, 205A, and 205B, internal paths 210, 210A, an 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

In some embodiments, enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post-analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule sample to arrive during a given operation cycle for any sample on track 200. A central controller, or controllers associated with modules themselves, can resolve any conflicts over a sample for given cycle. By giving a module prior knowledge of the arrival time of a sample, each module can prepare resources and interleave tests or portions of tests to more efficiently allot internal resources. In this manner, modules can operate on samples in a just-in-time manner rather than by using large physical buffers. The effect is that the virtual queue for a given module can be much larger than the physical capacity of the sub-path serving that module, and existing scheduling algorithms can be used. Effectively, each module can treat track 20 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepare and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle. It should further be appreciated that these scheduling techniques may be used locally within a workcell or globally, scheduling samples across multiple workcells, taking into account the transit time for traversing the inter-cell track.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for sample when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presume to be limited generally to sub-paths, there is no need to flush queues in other modules if a STAT sample does not need immediate access to those modules. Any additional modules that need to service a STAT sample on a subsequent cycle can flush their queues at that pair providing "just-in-time" access to a STAT sample without otherwise disrupting the operation of each analyzer module.

Modular design also allows certain other advantages. If the automation systems within an analyzer module are adapted to take advantage of the track system contained in the module, new features can be added that use the common track. For example a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module. In some embodiments, the inter-cell track can interface track 200, allowing the operator to load any reagents along with samples at a different workcell than the destination workcell for the reagent.

In some embodiments, the individual track portions shown in FIG. 3, and FIG. 2A and FIG. 2B can be operated independently from one another, or can be passive. Independent carrier movement provides advantages over friction-based track systems, such non-localized conveyor belts where the entire friction track must be moved to effect movement of a sample carrier. This means that other samples also on that track must move the same rate. This also means that if certain sections operate at different speeds, collisions between passive carriers carrying samples can occur.

FIG. 4A depicts an exemplary carrier 250 for use with some embodiments of the local automation systems. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255, such as a sample tube 255, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 25 are in a drawer or rack.

Figure 6:
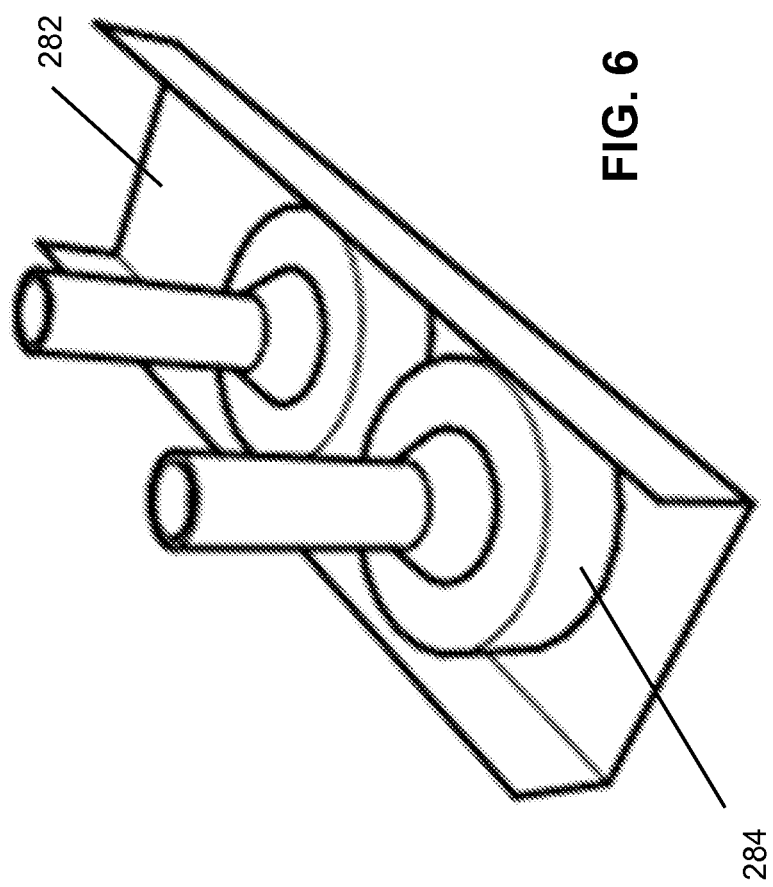
FIG. 6 is a perspective view of exemplary carriers for use with some embodiments disclosed herein.

In addition to sample carriers, such as carrier 250 in FIG. 4A, carriers can be any suitable carrier, such as prior art pucks or the carrier shown in FIG. 6.

Figure 4B:
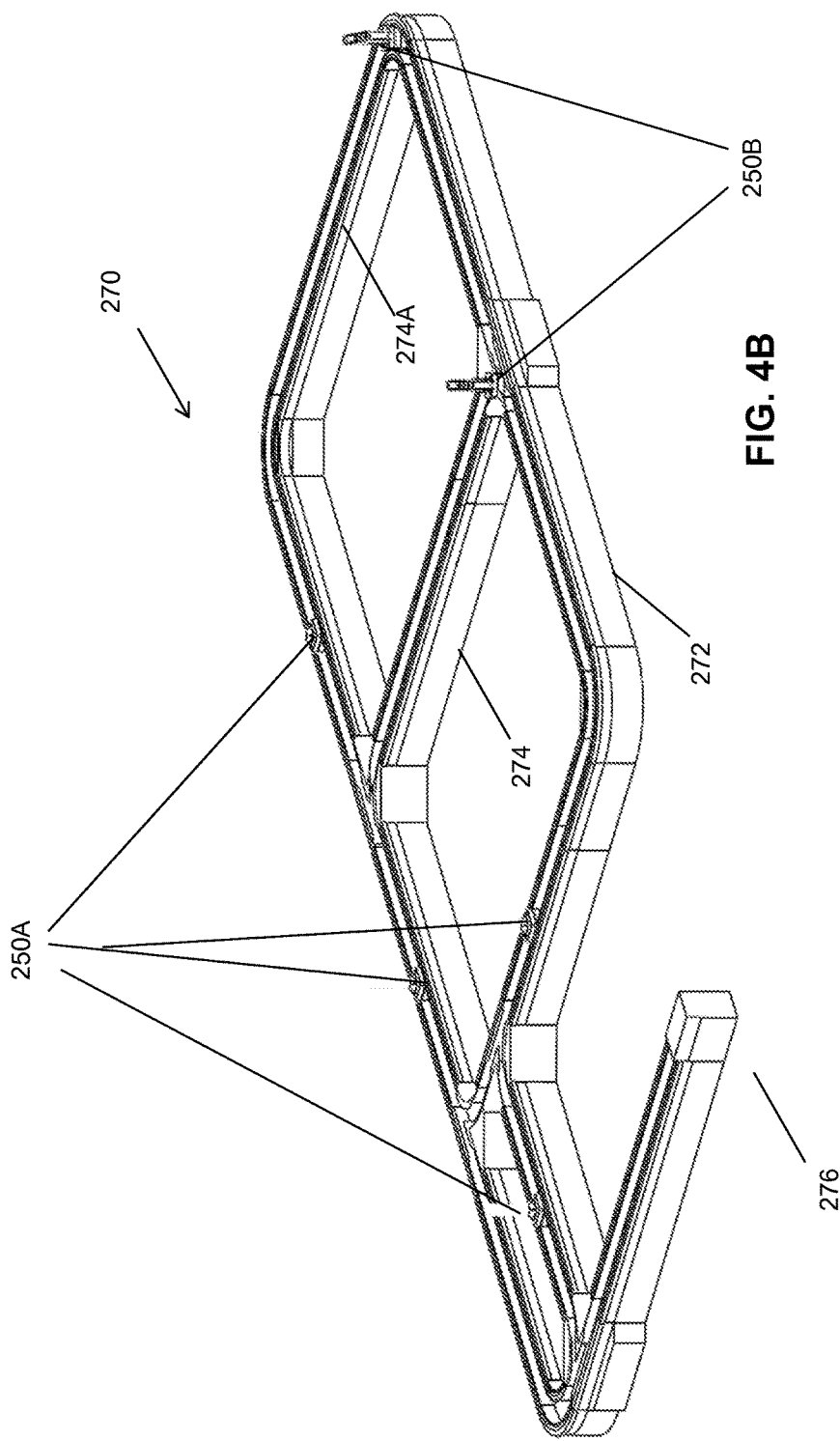
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 5:
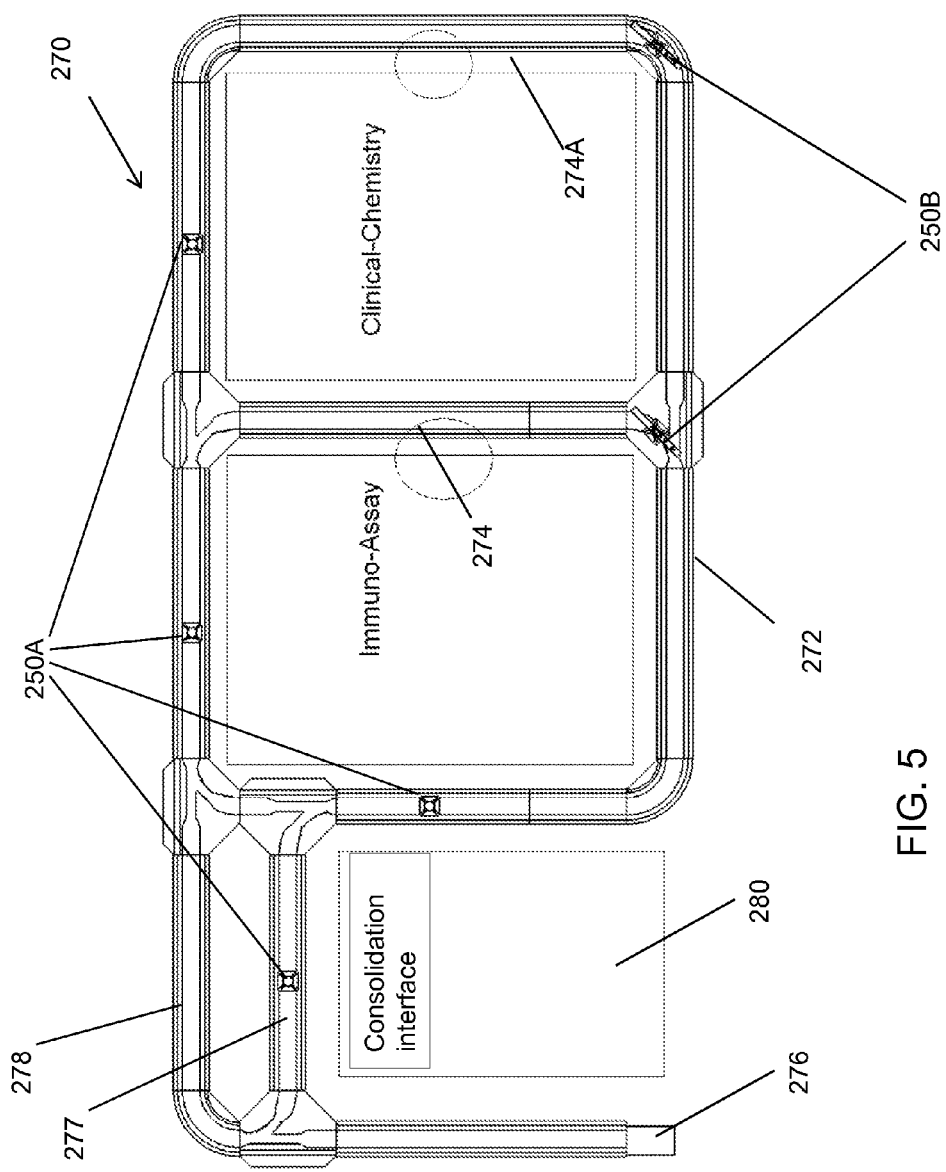
FIG. 5 is a top view of an exemplary automation systems carrier that can be used with the embodiments disclosed herein.

FIG. 5 shows an additional view of an exemplary track configuration 270. In this example, sub-path 274 serves an immunoassay station, while sub-path 274A serves a clinical chemistry station. Input/output lane 276 can interface the inter-cell track via consolidation interface 280. In some embodiments, consolidation interface 280 includes a plurality of locations into which inter-cell trays may be placed during loading and unloading operations. For example, in some embodiments, individual loading bays handled by consolidation interface 280 can hold different trays that have different destination workcells. This can allow the inter-cell track to send each tray directly to a destination, limiting the number of stops a tray needs to make to deliver all samples, which can ensure that trays are substantially full when they traverse the inter-cell track.

Consolidation interfaces may interact with different numbers of trays, depending on the routing across the inter-cell track used in each embodiment. For example, in some embodiments, each consolidation interface may have a loading area suitable for one tray. In these embodiments, trays may travel in a loop, stopping at each workcell, and swapping out those sample vessels destined for that workcell for sample vessels from that workcell. Trays may arrive empty at pre-analytic workcells. In some embodiments, several trays may fit in a loading area, allowing each tray to be destined for one workcell (or a group of workcells that perform load balanced execution of tasks. In some embodiments, there may be room for one tray to be loaded while another is unloaded, preventing consolidation interfaces from becoming bottlenecks.

Input/output lane 276 can be accessed by sub paths 277 and 278 to buffer samples for insertion or removal of the samples from the main track 272. The use of a buffer that is part of the local automation track can be helpful for ensuring that only substantially full trays are sent along the inter-cell track. In some embodiments, by utilizing buffers with each workcell, the number of trays needed may be reduced such that trays are only delivered to the output portion of consolidation interface 280 when a substantial number of samples are completed and ready to be sent to the next workcell.

In some embodiments, the consolidation interface 280 removes sample vessels from the carriers 250A and 250B and places them into the inter-cell trays, and vice versa. In some embodiments, the trays can hold samples in carriers and transport both the carriers and the sample vessels to the next workcell. In these embodiments, the trays act like ferries to shuttle local carriers in bulk to other workcells.

FIG. 6 depicts exemplary carriers may be used with certain workcells in some embodiments. In these embodiments, the carriers are passive pucks 284, which can traverse channel type track 282 within a local automation system. Track 282 can include a friction belt, or magnetic drive means to propel pucks 284 along the track. In some embodiments, pucks 284 may be loaded directly into inter-cell trays to go to another workcell. In some embodiments, samples may be removed from each puck and placed directly into a slot in an inter-cell tray to traverse the inter-cell track.

Figure 7:
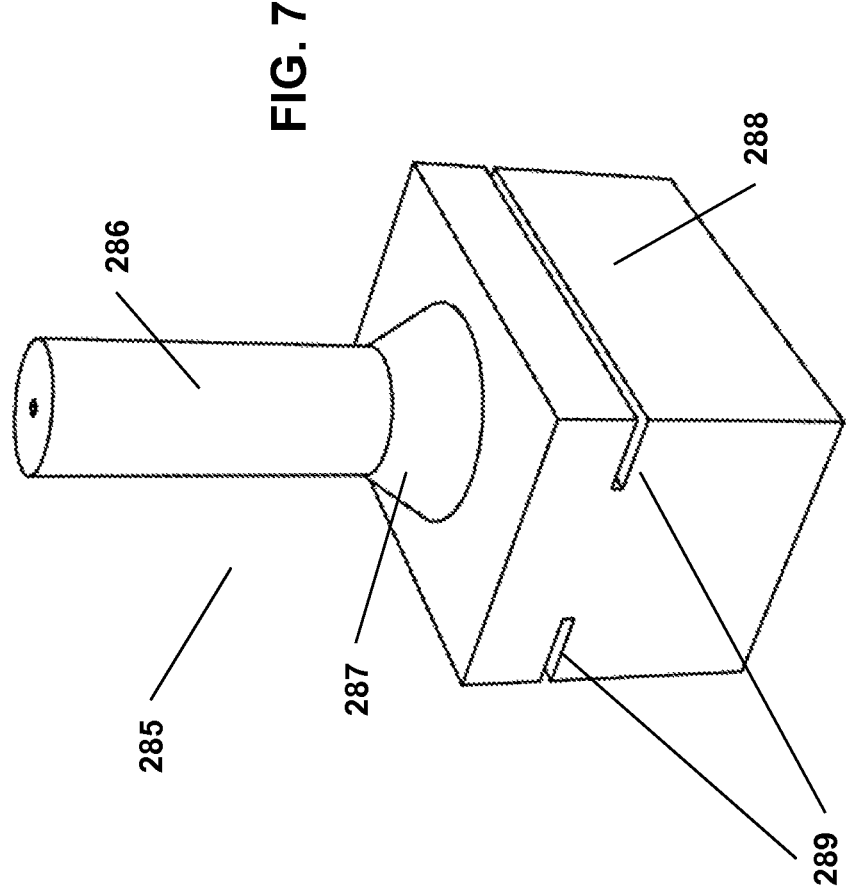
FIG. 7 is a perspective view of an exemplary carrier for use with some embodiments disclosed herein.

FIG. 7 depicts another exemplary carrier that may be used with certain workcells in some embodiments. Carrier 285 holds sample vessel 286 via a sample holder 287. Carrier body 288 may house internal components, such as onboard processors, RFID tags, memory, drive components, power sources, etc. Meanwhile, slots 289 in the side of the carrier body 288 can receive rails as part of a track. These slots may allow carrier 285 to be precisely directed via the rails of the track.

Inter-Cell Transportation

Figure 8:
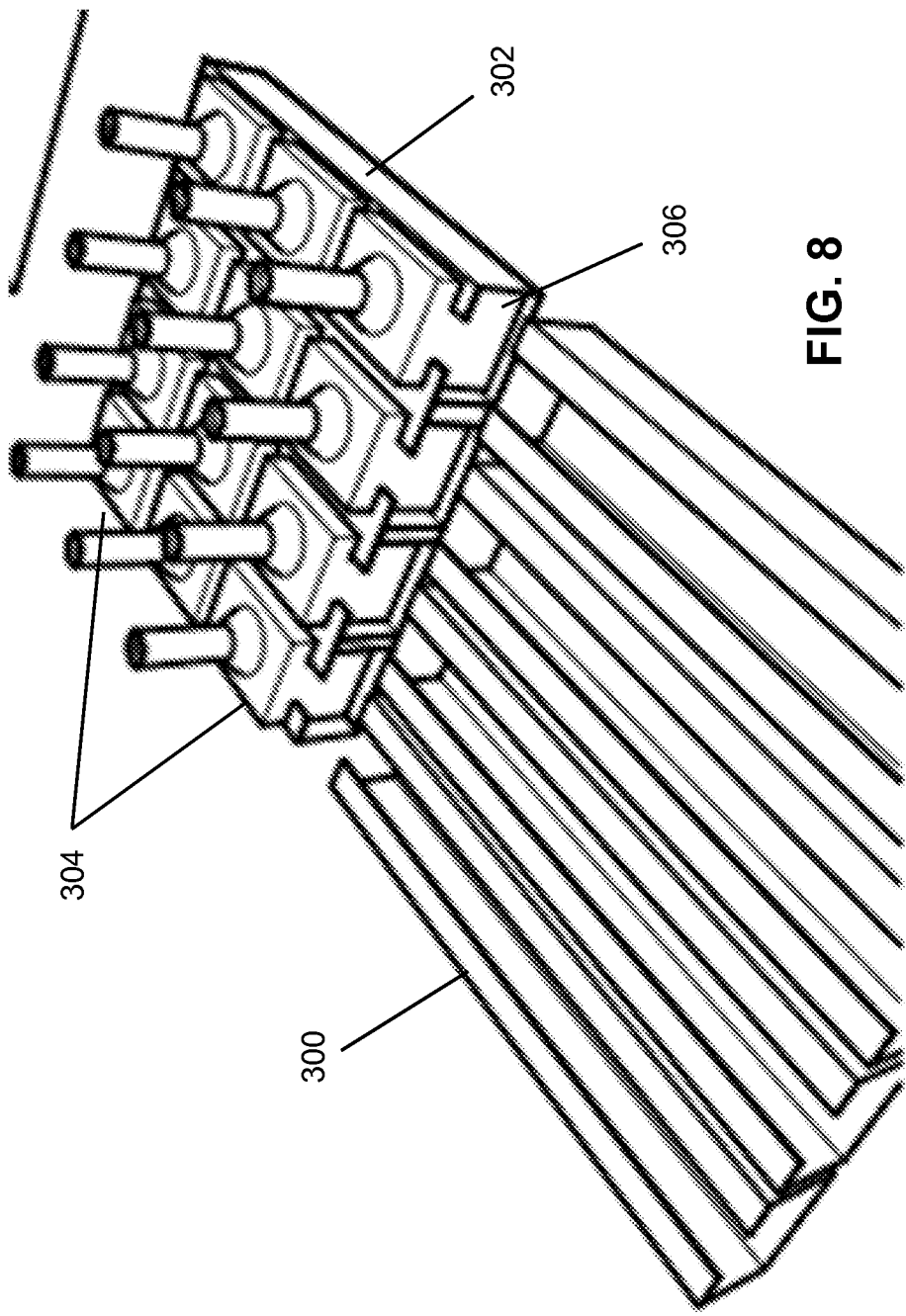
FIG. 8 is a perspective view of an exemplary consolidation interface for use with some embodiments disclosed herein.

FIG. 8 depicts an exemplary embodiment of a consolidation interface, whereby entire carriers are loaded into each inter-cell tray. Consolidation interface 300 includes a plurality of tracks onto which carriers, such as carrier 285 in FIG. 7, can be driven. A plurality of carriers 304 can be driven into consolidation interface 300 to prepare the carriers to be loaded into tray 302. Tray 302 may then be loaded with a plurality of carriers 304 by driving the carriers on to the tray, such as by driving carriers into slot 306. Once the carriers are driven into the tray and the tray is substantially full, the tray may be released into the inter-cell track to travel to the next workcell. The unloading process is the opposite of the loading process. Carriers 304 may be driven from tray 302 out of slots 306 into a consolidation interface 300 at the destination workcell. These carriers may then be driven from the consolidation interface 300 onto a local automation track to begin performing local tasks as part of the overall work-flow.

Figure 9:
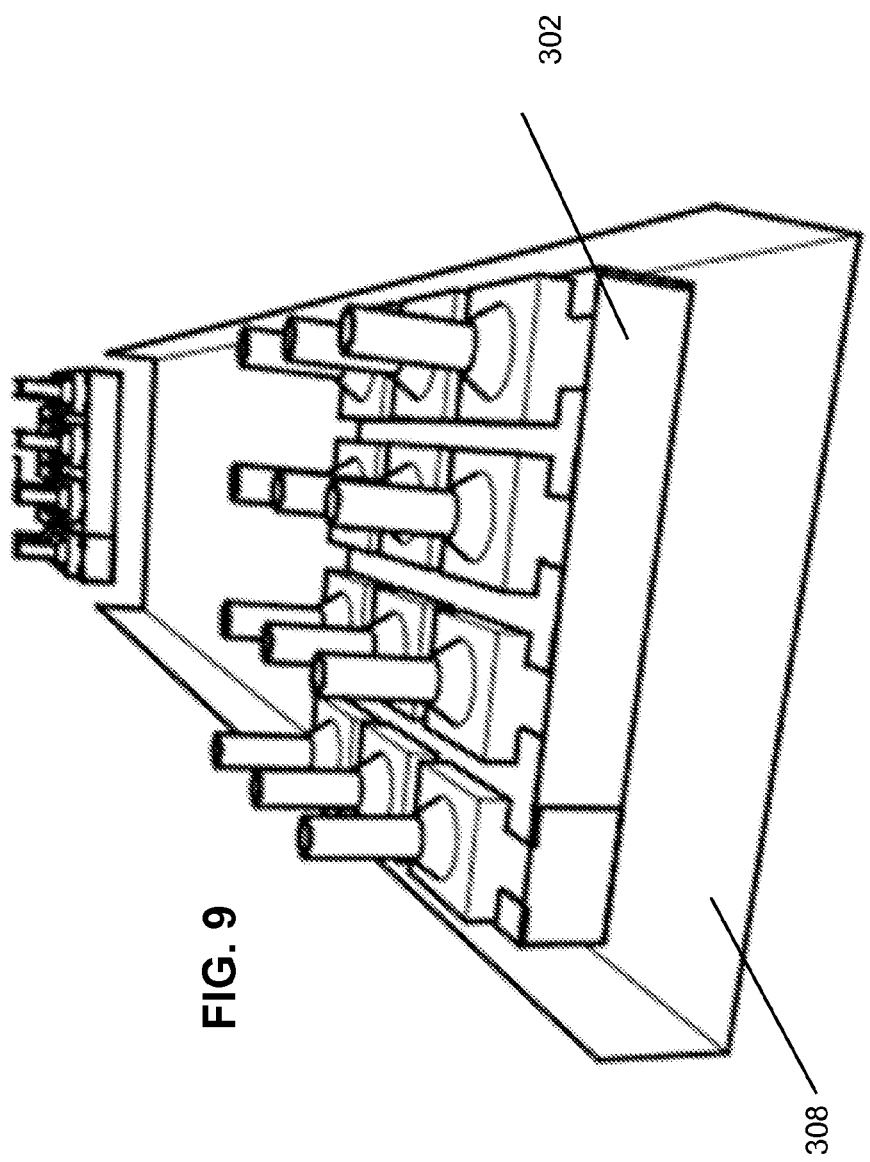
FIG. 9 is a perspective view of an exemplary section of an inter-cell track for use with some embodiments disclosed herein.

FIG. 9 shows an exemplary situation on an inter-cell track 308. Tray 302 may be driven along inter-cell track 308 via any conventional means, including a friction belt, magnetic drive, such as a linear synchronous motor, friction wheels. Tray 302 may also be self-propelled, such as by including an onboard motor and drive wheels. In this example, tray 302 includes a dozen carriers and sample vessels. However, it should be appreciated that any suitably sized trays may be used. In some embodiments, substantially more than a dozen (e.g., up to 50 or 100, etc.) sample vessels are loaded into a tray, such as tray 302. Track 30 may include branches, sections, turns, etc. and may be several meters long, allowing workcells to be separated by several meters if desired.

In some embodiments, where the inter-cell track traverses multiple rooms or floors in a large lab, vertical components, such as ramps and elevators may be incorporated into the inter-cell track for trays that need to go to a workcell that is at a different height from the source workcell. It should be noted, that the length of track 308 may add latency to the overall work-flow, but the throughput may be substantially improved by using trays and inter-cell tracks. In some embodiments, multiple inter-cell tracks may be used.

Figure 10:
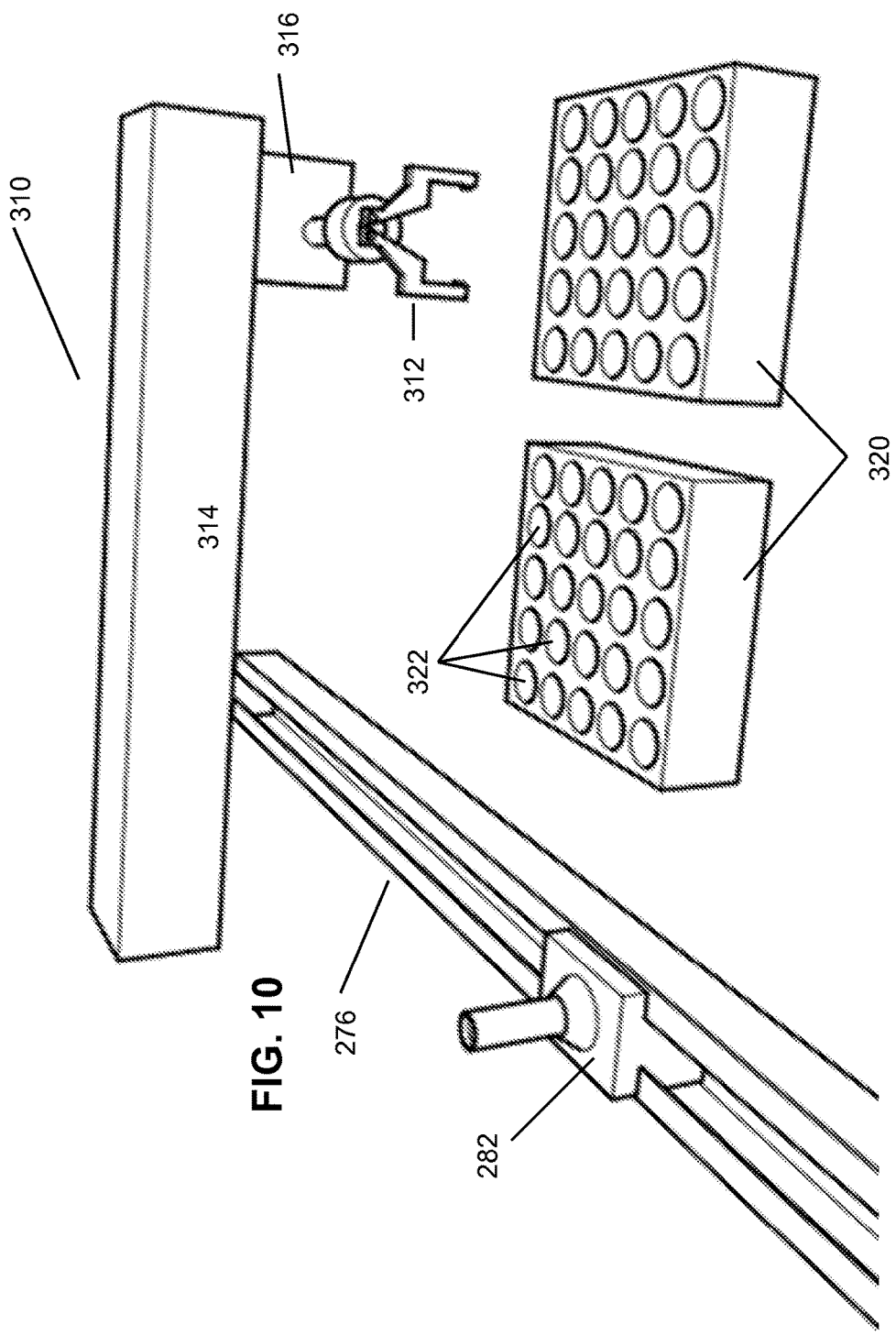
FIG. 10 is a perspective view of an exemplary consolidation interface for use with some embodiments disclosed herein.

FIG. 10 shows another embodiment of a consolidation interface 310. In this embodiment, sample vessels are removed from local carriers and placed into individual slots within inter-cell trays. This embodiment may be advantageous because a greater density of samples may be possible within inter-cell trays. In some embodiments, local carriers may be small enough that arrangements, such as shown in FIG. 8, can also achieve a high density of samples.

In this embodiment, sample carriers, such as carrier 282, travel along a local automation track, such as track 276. Consolidation interface 310 may be placed in a predetermined location within a local automation system, such that carrier 282 is only delivered to the consolidation interface when it is to be transferred into an inter-cell tray. Similarly, samples may be loaded into local carriers, such as carrier 282, when a tray arrives from the inter-cell track.

Consolidation interface 310 may include a sample handling robot arm that is suitable for grabbing, lifting, moving, and placing samples. Robot arm 312 may include any suitable design for grabbing sample vessels, such as a pincher type design depicted. Robot arm 312 may be attached to a carriage 316, which travels along a track 314. Carriage 316 may be moved horizontally and vertically using a drive mechanism, such as pneumatics, hydraulics, linear actuators, etc. Robot arm 312 may also be moved using an actuator or piston type device, which, along with the motion of carriage 316, enables robot arm 312 can be moved in three dimensions to allow samples to be grabbed lifted moved and placed. In some embodiments, robot arm 312 may be moved using an articulated arm having joints, rather than attached to a moving carriage 316. The term robot arm may also refer to the overall system, comprising end effectors and motion devices that allow the robot arm to move, such as items 312, 316, and 314 collectively.

Trays 320 can be placed within the reach of robot arm 312 in the loading area of consolidation interface 310. A loading area may have room for multiple trays, in some embodiments allowing robot arm 312 to load multiple trays (such as multiple single-destination trays) simultaneously. In some embodiments, the loading area may also include at least an input area and an output area. This may allow trays to arrive while another tray is being loaded. This may allow greater efficiency as robot arm 312 may move into the loading area to place a sample vessel in an outgoing tray and, before returning to track 276, the robot arm may pick up another sample from a recently received full tray.

Trays 320 can include a plurality of slots 322. The slots may be of suitable size to gently hold sample vessels. Sample vessels may be held tightly enough to be stabilized while the trays 320 traverse the inter-cell track, but still loosely enough to be easily removed by a robot arm. In this example, 25 slots are placed in a 5×5 array. This can allow a reduction in traffic on the inter-cell track versus a single-sample-per-carrier track of 25:1. This may allow the inter-cell track to operate substantially slower than may be desired for local automation tracks.

Figure 11:
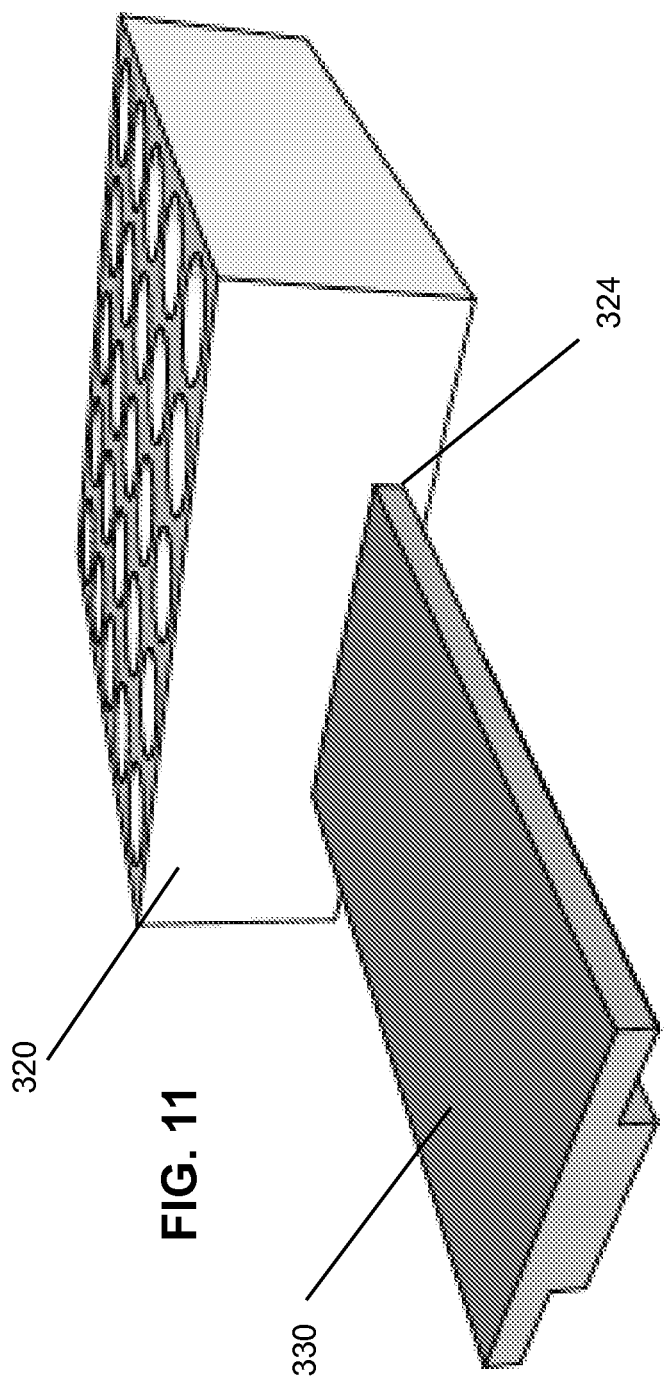
FIG. 11 is a perspective view of an exemplary section of an inter-cell track for use with some embodiments disclosed herein.

FIG. 11 depicts an embodiment of an inter-cell track that may allow trays to securely transit the inter-cell track. In this embodiment, the inter-cell track is a rail 330. Each of trays 320 can include a correspondingly shaped recess 324, which enables the tray to securely hold track 330. Trays 320 may drive along the rail 330 using any conventional means, including magnetic drives or friction drives, and the like.

Workcells

Figure 12:
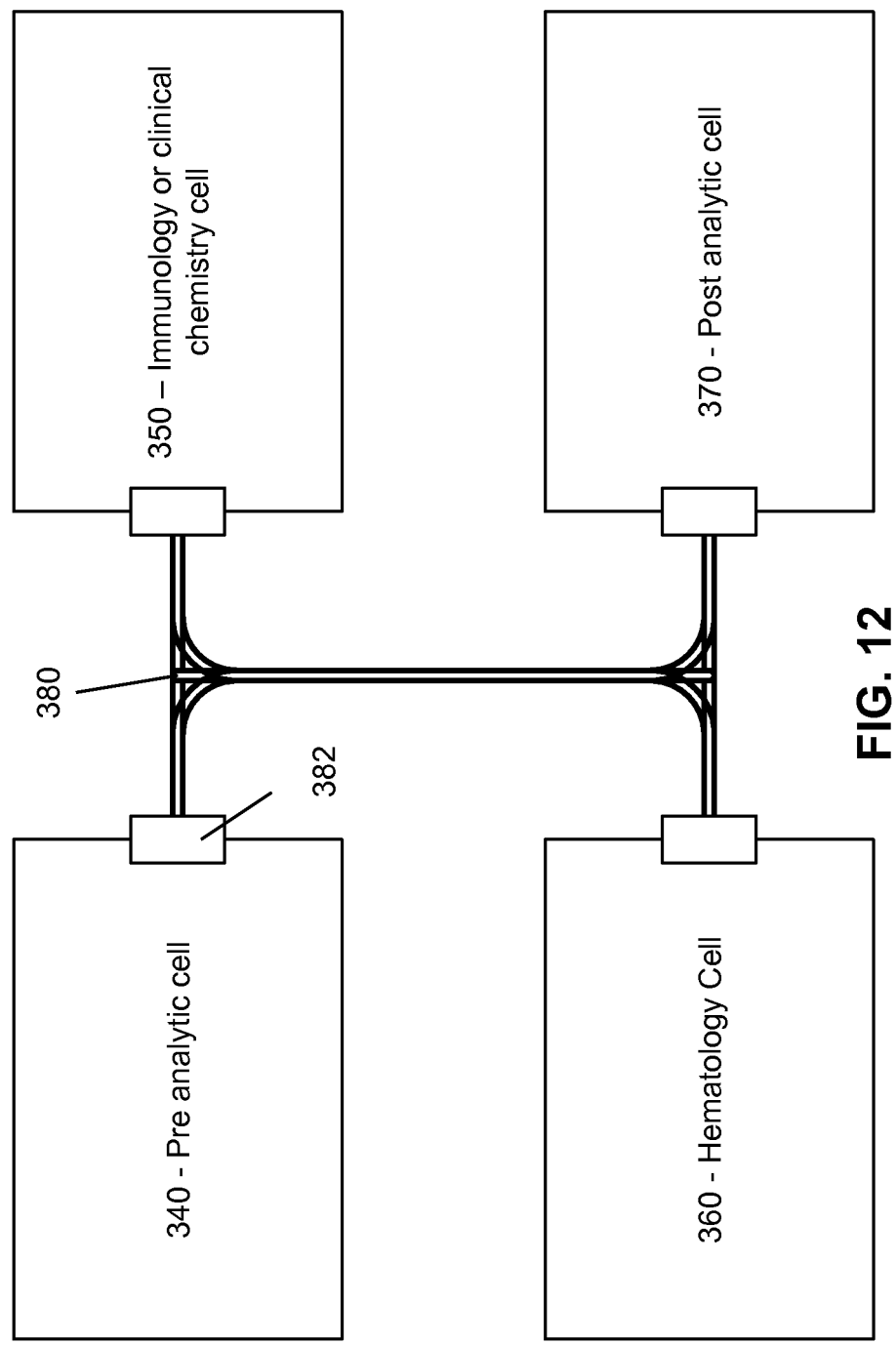
FIG. 12 is a system diagram of an exemplary workcell based automation system.

FIG. 12 depicts an exemplary arrangement of workcells laboratory environment. The system includes a pre-analytic cell 340, an immunology and/or clinical chemistry cell 350, a hematology cell 360, and a post-analytic cell 370. These workcells an connected via an inter-cell track 380. It should be appreciated that, in some embodiments, additional workcells can be used for additional tasks and any of the workcells in FIG. 12 can be replicated for load balancing.

Workcells interact with the inter-cell track 380 via consolidation interface 382. Consolidation interface 382 can utilize any of the mechanisms for transferring samples to and from trays that are described throughout this application. Trays carrying carriers and/or sample vessels can be loaded and unloaded via consolidation interfaces to transport fluid samples from one workcell to another. The basic work-flow for each sample in this example would include preprocessing at pre-analytic cell 340 followed by diagnostic testing using immunology or clinical chemistry cell 350 and/or hematology cell 360. Depending on the sample, it may be necessary to send the sample to multiple workcells as part of a work-flow. When a sample leaves pre-analytic cell 340, it may be placed into a tray destined for immunology or chemistry cell 350 or onto a tray destined for hematology workcell 360. Samples leaving analytic workcells 350 and 360 may be destined for post-analytic workcell 370 or destined for another analytic workcell 360 or 350. In some embodiments, load balancing can be performed using multiple instances of analytic workcells, such as multiple instances of immunology and clinical chemistry workcell 350. Within each workcell, multiple stations may be employed to perform specific subtasks or to load-balance tasks.

Figure 13:
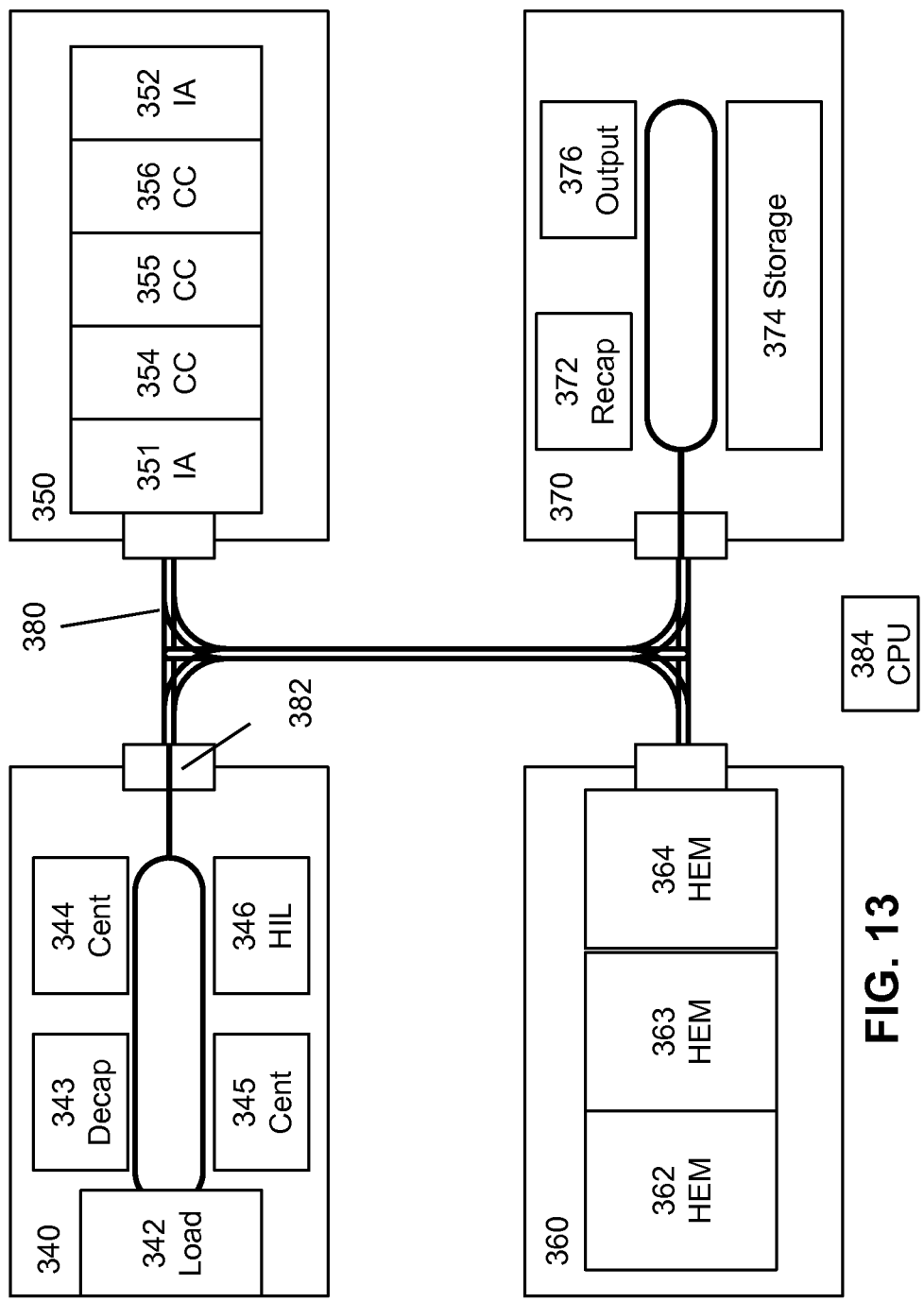
FIG. 13 is a system diagram of an exemplary workcell based automation system.

FIG. 13 shows an exemplary workcell system, like that depicted in FIG. 12, with more detail about the individual stations and automation systems used within each workcell. In this example, pre-analytic workcell 340 includes a plurality of individual stations designed to perform pre-analytic tasks. Station 342 is a loading station designed to receive wire trays of samples from a refrigerated area that may be placed there by hand by a operator. Depending on the type of sample, centrifuging may be necessary. Because centrifuging may be a slow process, there may be multiple instances of centrifuging stations within a workcell, including centrifuge 344 and centrifuge 345. Samples typically arrive with plastic caps that seal the sample from foreign agents and to prevent spilling in the lab. De-capper 343 can be used to automate the task of removing the cap to prepare the sample to be accessed using pipettes. For hematology samples, such as whole blood samples, a Hemolysis, Icterus, Lipemia (HIL) station 346 may be employed to perform sample integrity checking prior to analytical testing, such as detecting blood clots. All of the stations within pre-analytic cell 340 may be accessed using a friction-based automation track that maneuver samples in passive pucks in a FIFO manner.

Immunoassay and clinical chemistry workcell 350 may use a different automation system. Workcell 350 may include various immunoassay stations 351 and 352 and various clinical chemistry analysis stations, 354, 355, and 356. The number of individual stations making up cell 350 may be selected based on the type of expected testing in the lab. This may allow increased throughput for each type of tests. In addition, cell 350 may be expandable, allowing a lab to add additional stations as more throughput is needed, as a lab grows in scale. The automation system used in cell 350 may be any of those described throughout, including the automation system depicted in FIG. 3, which may use intelligent autonomous carriers to provide high-speed random access to samples within cell 350.

Hematology workcell 360 can include a plurality of hematology testing stations 362, 363, and 364. The automation system used within hematology workcell 360 may be any of those discussed throughout, including the automation system depicted in FIG. 3, and may utilize autonomous intelligent carriers. The number of hematology cells include may be selected based on expected throughput requirements. Hematology workcell 360 may be expandable by adding additional hematology analysis testing stations as a laboratory grows.

Post-analytic cell 370 can include multiple stations for performing post-analytic tasks. Samples may be recapped by recapper 372 and may be moved into a storage area 374, which may include a refrigerated area. Samples may be retrieved from post-analytic cell 370 via output area 376. Samples may then be handled by hand and disposed of or placed into additional storage.

CPU 384 can act as a scheduler/traffic manager for the automation system as a whole, including trays on track 380. CPU 384 can include a controller that directs mechanisms to move samples onto and off of track 380 via interface 382 (including loading and unloading samples from trays). Once trays are loaded, they may wait for track 380 or portions of track 380 to allow them to move from one workcell to another. CPU 384 may act as a scheduler to orchestrate this traffic management. CPU 384 may also communicate with CPUs that are part of workcells 340, 350, 360, and 370. This may allow coordination of scheduling, when samples will be loaded and unloaded from trays, and when they will be transferred from one workcell to another. This may allow a plan to be created for each sample as it enters the system via load station 342. In some embodiments, CPU 384 may work with local processors to determine exactly which stations each sample will visit and when the sample will arrive at those stations. Certain samples, such as STAT samples, can be given higher priority and be put at the head of each queue in the system so that STAT samples are processed first at each workcell and are the first samples to be placed onto outgoing trays on the inter-cell track.

Figure 14:
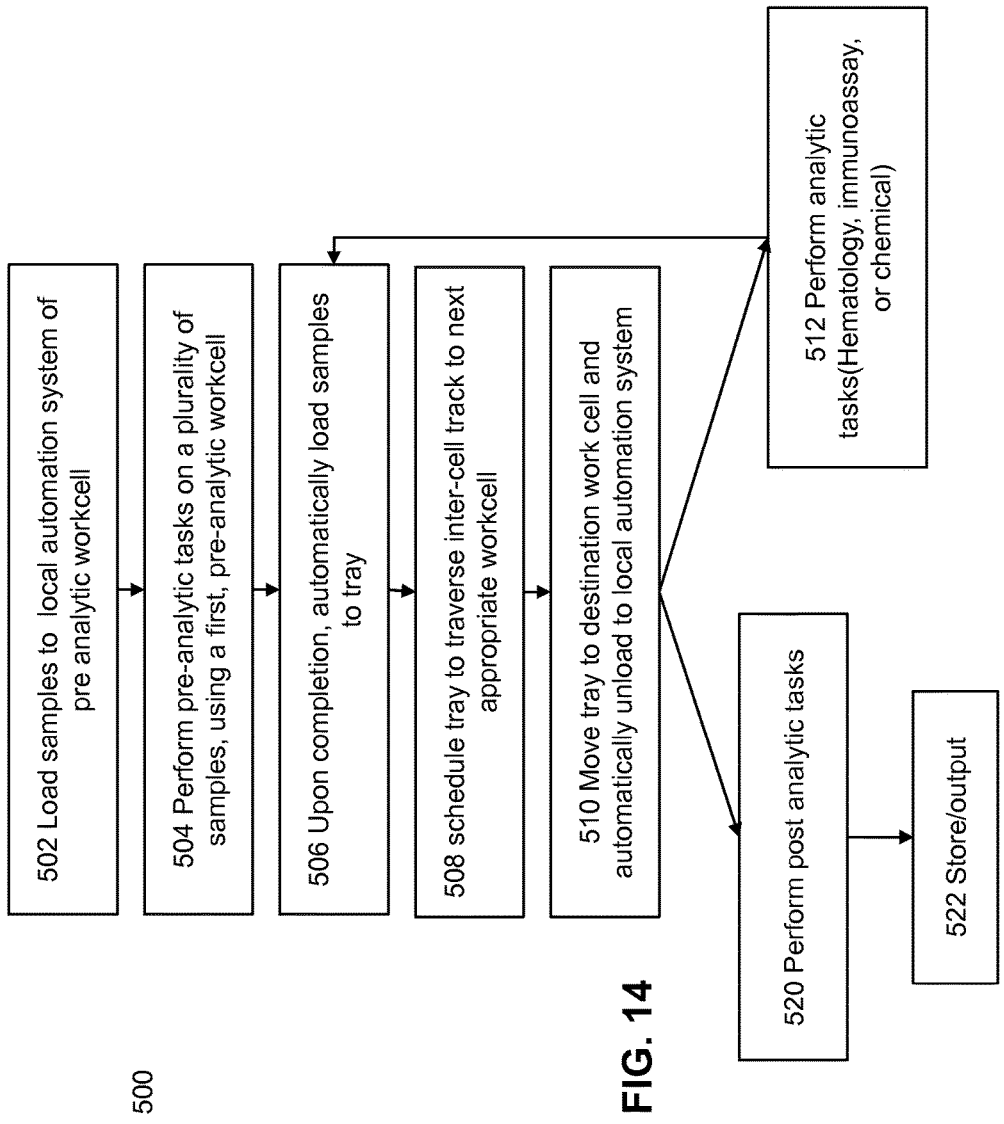
FIG. 14 is a flow chart of an exemplary workcell based automation system.

FIG. 14 shows work-flow 500, which may be used to handle samples in a workcell-based automation system. At step 502, samples are loaded onto the local automation system of a pre-analytic workcell. At step 504, the pre-analytic workcell will perform pre-analytic tasks on the sample, such as decapping the sample, adding stabilizing agents, centrifuging the sample, etc. At step 506, upon completion of pre-analytic tasks, the local automation system to the pre-analytic workcell will make the sample available to a consolidation interface for the workcell. This can include moving a sample carrier holding the sample vessel to a track section that is accessible to a consolidation interface. The consolidation interface will then either move the carrier or remove the sample vessel from the carrier and place the sample into a tray on the inter-cell track.

At step 508, the central scheduler for inter-cell track will direct the tray to traverse the inter-cell track without colliding with other trays. This may include waiting for track sections to clear or choosing unoccupied track sections to send the tray along. At step 510, the tray is moved along the inter-cell track to the next workcell of the work-flow. After a pre-analytic step, the next appropriate workcell will generally be an analytic workcell, such as workcell 350 or 360. Upon reaching the destination workcell, the local consolidation interface will move each sample in the tray that is to be processed at the workcell from the tray and place the sample into the local automation system for the workcell.

At step 512, an analytic task will be performed on each sample delivered to an analytic workcell. Upon completion of analytic tasks on the sample, the sample is delivered back to the consolidation interface for the workcell so that the sample can be loaded back into a tray to traverse the inter-cell track. The method then repeats back at step 506.

Once the analytic tasks are completed for a sample, at step 510, the destination workcell will be a post-analytic workcell. In some embodiments, that will generally be the final workcell that the sample will visit. When the sample arrives at a post-analytic workcell at step 510, method 500 proceeds to step 520. At step 520, the post-analytic workcell will perform any necessary post-analytic tasks on the sample, including recapping the sample. At step 522, the post-analytic workcell stores the sample in local storage or moves the sample to an output lane to be collected by an operator.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A system for performing in-vitro diagnostics (IVD) on a plurality of patient samples in a plurality of patient sample vessels, comprising:
   a plurality of workcells including each of the following workcells:
      a pre-analytic workcell comprising at least one pre-analytic station including one of a decapper, a centrifuge, and a Hemolysis, Icterus, Lipemia (HIL) station,
      an analytic workcell comprising a plurality of automated analyzer stations, each analyzer station being one of a hematology analyzer, a clinical chemistry analyzer, and an immunoassay analyzer, and
      a post-analytic workcell comprising at least one post-analytic station including one of a capper and a storage area configured to store the patient sample vessels,
      wherein each workcell includes an internal automation system comprising an external workcell interface, an internal track, and a plurality of carriers that are together configured to move the patient sample vessels between the stations and the external workcell interface;
   at least one inter-cell tray configured to hold multiple of the plurality of patient sample vessels for transport between the plurality of workcells; and
   an inter-cell track configured to transport the at least one inter-cell tray along one or more paths between the external workcell interfaces of the plurality of workcells,
   wherein the external workcell interface of each workcell comprises a robot arm configured to load the plurality of patient sample vessels under processor control from the internal track to the at least one inter-cell tray for processing by another of the plurality of workcells, and to move the plurality of patient sample vessels under processor control from the at least one inter-cell tray to the internal automation system for processing by each workcell.

2. The system of claim 1, wherein each robot arm of each workcell is configured to remove the patient sample vessels from the plurality of carriers and place the vessels into the at least one inter-cell tray.

3. The system of claim 1, wherein the at least one inter-cell tray is configured to hold a first maximum number of vessels and each carrier is configured to hold a second maximum number of vessels, which is less than the first maximum number of vessels.

4. The system of claim 1, wherein the at least one inter-cell tray is configured to hold the plurality of carriers and to transfer the plurality of carriers along the inter-cell track.

5. The system of claim 1, wherein the at least one inter-cell tray comprises a plurality of inter-cell trays.

* * * * *